(12) United States Patent
Venkatraman et al.

(10) Patent No.: US 11,154,284 B2
(45) Date of Patent: Oct. 26, 2021

(54) OCCLUSION DEVICE FOR CLOSING ANATOMICAL DEFECTS

(75) Inventors: Subramanian Venkatraman, Singapore (SG); Yin Chiang Freddy Boey, Singapore (SG); Laximikant Khanolkar, Singapore (SG); Prasada Rao, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 189 days.

(21) Appl. No.: 14/233,132

(22) PCT Filed: Jul. 16, 2012

(86) PCT No.: PCT/SG2012/000252
§ 371 (c)(1),
(2), (4) Date: May 30, 2014

(87) PCT Pub. No.: WO2013/012392
PCT Pub. Date: Jan. 24, 2013

(65) Prior Publication Data
US 2014/0296798 A1 Oct. 2, 2014

Related U.S. Application Data

(60) Provisional application No. 61/508,209, filed on Jul. 15, 2011.

(51) Int. Cl.
*A61B 17/00* (2006.01)
*A61L 31/16* (2006.01)

(52) U.S. Cl.
CPC .......... *A61B 17/0057* (2013.01); *A61L 31/16* (2013.01); *A61B 2017/00004* (2013.01);
(Continued)

(58) Field of Classification Search
CPC .......... A61B 17/0057; A61B 17/12022; A61B 17/12027; A61B 17/12031;
(Continued)

(56) References Cited

U.S. PATENT DOCUMENTS 5,669,933 A * 9/1997 Simon ........................ A61F 2/01
600/191
5,702,421 A * 12/1997 Schneidt ............ A61B 17/0057
600/32

(Continued)

FOREIGN PATENT DOCUMENTS

DE  20 2010 011 724 U1  12/2010
WO     2004/012603 A2    2/2004
(Continued)

OTHER PUBLICATIONS

Cambier et al., "Percutaneous Closure of the Small (<2.5 mm) Patent Ductus Arteriosus Using Coil Embolization," *American Journal of Cardiology* 69:815-816, 1992.
(Continued)

*Primary Examiner* — Jing Rui Ou
(74) *Attorney, Agent, or Firm* — Seed Intellectual Property Law Group LLP

(57) ABSTRACT

An occlusion device for closing an anatomical defect in tissue comprising a conduit connecting an opening on a first tissue and an opening on a second tissue is provided. The occlusion device comprises a scaffold comprising a) a proximal support structure comprising at least two arms; b) a distal support structure comprising at least two arms, wherein the arms are adapted to provide anchorage for the device in the tissue; and c) a waist portion adapted for extending through the opening on the first tissue and connecting the proximal support structure with the distal support structure, wherein the scaffold consists essentially of a biodegradable polymer, wherein the proximal support struc-
(Continued)

ture and the distal support structure comprise or consist of polycaprolactone (PCL), poly-(D,L-lactide-co-caprolactone) (PLC), or a mixture thereof. A method of closing an anatomical defect using the occlusion device is also provided.

33 Claims, 8 Drawing Sheets

(52) U.S. Cl.
CPC ............ *A61B 2017/00592* (2013.01); *A61B 2017/00597* (2013.01); *A61B 2017/00615* (2013.01); *A61B 2017/00623* (2013.01)

(58) Field of Classification Search
CPC .......... A61B 17/12036; A61B 17/1204; A61B 17/12099; A61B 17/12122; A61B 2017/00575; A61B 2017/00578; A61B 2017/00592; A61B 2017/0061; A61B 2017/00615; A61B 2017/00628; A61B 2017/00632; A61B 2017/00637; A61B 2017/00641; A61B 2017/00646; A61B 2017/00659; A61B 2017/00004; A61B 2017/00579; A61B 2017/00597; A61B 2017/00623; A61F 2230/0039; A61F 2230/0047; A61F 2230/0058; A61F 2230/006; A61F 2230/0093; A61L 15/54; A61L 31/16

See application file for complete search history.

(56) References Cited

U.S. PATENT DOCUMENTS

| | | | | |
|---|---|---|---|---|
| 6,080,182 | A * | 6/2000 | Shaw ................. | A61B 17/0057 128/887 |
| 6,143,037 | A | 11/2000 | Goldstein et al. | |
| 9,005,242 | B2 * | 4/2015 | Cahill ............... | A61B 17/0057 606/215 |
| 2001/0037129 | A1 * | 11/2001 | Thill ................. | A61B 17/0057 606/213 |
| 2003/0057156 | A1 * | 3/2003 | Peterson .......... | A61B 17/12022 210/645 |
| 2003/0220667 | A1 * | 11/2003 | van der Burg ..... | A61B 17/0057 606/200 |
| 2004/0225324 | A1 * | 11/2004 | Marino .............. | A61B 17/0057 606/213 |
| 2005/0038470 | A1 * | 2/2005 | van der Burg ..... | A61B 17/0057 606/213 |
| 2005/0070957 | A1 | 3/2005 | Das | |
| 2005/0113868 | A1 | 5/2005 | Devellian et al. | |
| 2005/0192627 | A1 * | 9/2005 | Whisenant ......... | A61B 17/0057 606/213 |
| 2006/0122647 | A1 * | 6/2006 | Callaghan .......... | A61B 17/0057 606/213 |
| 2007/0073337 | A1 * | 3/2007 | Abbott ............... | A61B 17/0057 606/213 |
| 2007/0106327 | A1 * | 5/2007 | Thill ................. | A61B 17/0057 606/213 |
| 2007/0118176 | A1 * | 5/2007 | Opolski ............. | A61B 17/0057 606/213 |
| 2007/0167981 | A1 * | 7/2007 | Opolski ............. | A61B 17/0057 606/213 |
| 2007/0198059 | A1 * | 8/2007 | Patel ................. | A61B 17/0057 606/213 |
| 2007/0225756 | A1 * | 9/2007 | Preinitz ............. | A61B 17/0057 606/213 |
| 2008/0249562 | A1 * | 10/2008 | Cahill ................ | A61B 17/0057 606/215 |
| 2009/0082804 | A1 * | 3/2009 | Kato ................. | A61B 17/0057 606/213 |
| 2010/0106178 | A1 | 4/2010 | Obermiller et al. | |
| 2011/0184439 | A1 * | 7/2011 | Anderson .......... | A61B 17/0057 606/151 |

FOREIGN PATENT DOCUMENTS

| | | |
|---|---|---|
| WO | 2008/024491 A1 | 2/2008 |
| WO | 2011/096896 A1 | 8/2011 |

OTHER PUBLICATIONS

Chen et al., "Transcatheter Amplatzer Occlusion and Surgical Closure of Patent Ductus Arteriosus: Comparison of Effectiveness and Costs in a Low-Income Country," *Pediatric Cardiology* 30:781-785, 2009.
Choi et al., "The Results of Transcatheter Occlusion of Patent Ductus Arteriosus: Success Rate and Complications Over 12 Years in a Single Center," *Korean Circulation Journal* 40:230-234, 2010.
Clyman "Recommendations for the postnatal use of indomethacin: An analysis of four separate treatment strategies," *Journal of Pediatrics* 128:601-607, 1996.
Hoffman et al., "Prevalence of congenital heart disease," *American Heart Journal* 147:425-439, 2004.
Hoffman et al., "The Incidence of Congenital Heart Disease," *Journal of the American College of Cardiology* 39:1890-1900, 2002.
Hosking et al., "Transcatheter Occlusion of the Persistently Patent Ductus Arteriosus: Forty-month Follow-up and Prevalence of Residual Shuntin," *Circulation* 84:2313-2317, 1991.
Kumar et al., "Percutaneous Occlusion of Patent Ductus Arteriosus with Controlled-Release Coil," *Asian Cardiovascular and Thoracic Annals* 7:204-208, 1999.
Latson et al., "Endocarditis Risk of the USCI PDA Umbrella for Transcatheter Closure of Patent Ductus Arteriosus," *Circulation* 90:2525-2528, 1994.
Masura et al., "Cathether Closure of Moderate- to Large-Sized Patent Ductus Arteriosus Using the New Amplatzer Duct Occluder: Immediate and Short-Term Results," *Journal of the American College of Cardiology* 31:878-882, 1998.
Moore et al., "The Duct-Occlud Device: Design Clinical Results, and Future Directions," *Journal of Interventional Cardiology* 14:231-238, 2001.
Mosalli et al., "Role of prophylactic surgical ligation of patent ductus arteriosus in extremely low birth weight infants: Systematic review and implications for clinical practice," *Annals of Pediatric Cardiology* 2:120-126, 2009.
Nora "Multifactorial Inheritance Hypothesis for the Etiology of Congenital Heart Diseases: The Genetic-Environmental Interaction," *Circulation* 38:604-617, 1968.
Pass et al., "Multicenter USA Amplatzer Patent Ductus Arteriosus Occlusion Device Trial: Initial and One-Year Results," *Journal of the American College of Cardiology* 44:513-519, 2004.
Portsmann et al., "Catheter Closure of Patent Ductus Arteriosus; 62 Cases Without Thoracotomy," *Radiologic Clinics of North America* 9:203-213, 1971.
Prieto et al., "Comparison of Cost and Clinical Outcome Between Transcatheter Coil Occlusion and Surgical Closure of Isolated Patent Ductus Arteriosus," *Pediatrics* 101:1020-1024, 1998.
Rashkind, "Nonsurgical closure of patent ductus arteriosus: clinical application of the Rashkind PDA Occluder System," *Circulation* 75:583-592, 1987.
Schneider et al., "Patent Ductus Arteriosus," *Circulation* 114:1873-1882, 2006.
Wessel et al., "Outpatient closure of the patent ductus arteriosus" *Circulation* 77:1068-1071, 1988.
Wu et al., "Common Congenital Heart Disorders in Adults," *Current Problems in Cardiology* 29:641-700, 2004.

* cited by examiner

OCCLUSION DEVICE FOR CLOSING ANATOMICAL DEFECTS

CROSS-REFERENCE TO RELATED APPLICATIONS

This application makes reference to and claims the benefit of priority of an application for "Devices, Delivery System and Methods for Percutaneous Treatment of Patent Ductus Arteriosus (PDA)" filed on Jul. 15, 2011, with the United States Patent and Trademark Office, and there duly assigned Ser. No. 61/508,209. The content of said application filed on Jul. 15, 2011, is incorporated herein by reference in its entirety for all purposes.

TECHNICAL FIELD

The invention generally relates to the field of transcatheter device closure techniques for closing an opening in a tissue and more particularly, to occlusion devices for closing anatomical defects in tissue and methods of closing an anatomical defect in tissue.

BACKGROUND

Defects in tissue are often combined with an opening in a tissue such as in the blood vessel wall and organ tissues, like the septum in the heart of mammals, for example, patent ductus arteriosus (PDA) as shown in FIG. 1.

FIG. 1 is a schematic diagram showing a comparison between (A) a normal heart, and (B) a heart with patent ductus arteriosus.

The ductus arteriosus is a blood vessel that connects a baby's aorta and pulmonary artery while the baby is in the womb. This connection allows blood to be pumped from the right side of the heart straight to the aorta, without passing by the lungs for oxygen. After birth, as the baby breathes on his or her own, the pulmonary artery opens to allow blood into the lungs, and the ductus arteriosus closes. Typically, it takes about four to seven days for the ductus arteriosus to be fully closed after birth.

In the event the ductus arteriosus does not close after birth as it should, a condition known as patent ductus arterious (PDA) results. PDA leads to abnormal blood flow between the aorta and pulmonary artery, two major blood vessels that carry blood from the heart. If left uncorrected, patency may lead to pulmonary hypertension and possibly congestive heart failure and cardiac arrhythmias. It affects approximately 40% to 50% of preterm infants born at less than 29 weeks of gestation and/or weighing less than 1.5 kg at birth. For children who were born at full term, the incidence of PDA has been reported to be approximately 1 in 2000 births. As can be seen, prematurity increases the incidence of PDA, and this is related to the physiological factors related to prematurity instead of the inherent abnormality of the ductus. PDA is also common in infants who have genetic conditions. In a family having 1 sibling with a PDA, there is approximately 3% chance of a PDA in a subsequent offspring. Reports have also shown a high incidence of PDA in infants whose mothers had rubella infection during their pregnancy.

Presently, there exist several strategies for treatment of a PDA. For preterm infants, medical or surgical interventions are the choices of treatment of PDA. For full term infants or older children, surgical or transcatheter closure procedures are used for treating PDA.

For medical intervention, indomethacin or ibuprofen are prescribed to help close the PDA by stimulating the PDA to constrict thereby closing the 'opened' ductus arteriosus. When medical intervention fails, surgical ligation of a PDA may be performed.

For surgical options, one form of direct interventional therapies for PDA is to stitch the PDA with medical suture or with a biocompatible material. Work has been carried out in these areas to facilitate these therapies. However, as these therapies require open-heart surgery, they are generally carried out when the size of the conduit is too small to allow a sheath to pass through. Furthermore, as such therapies are very invasive, they are extremely difficult to perform and require long hospitalization for patient recovery.

Given the greater pain and morbidity associated with surgical options, transcatheter closure of PDA has gained popularity, and complete closure rates at follow-up generally achieve at least 90% to 95% in most studies. In addition, transcatheter closure is often done on an outpatient basis, which allows the patient to go home on the day at which the procedure is done.

Most of the available transcatheter devices comprise non-degradable metals such as gold, titanium alloy, nitinol, stainless steel, a combination of these materials, or one or more similarly non-degradable materials such as Dacron or ePTFE. The implant device exists inside the patient's PDA permanently, which results in unease for the patient, as well as allergy and long-term toxicity risk. Metal-rich devices are also related to problems like friction lesions, perforations, erosion and thromboembolism.

In view of the above, there remains a need for an improved occlusion device for closing an anatomical defect in a tissue that addresses at least some of the above-mentioned problems.

SUMMARY OF THE INVENTION

In a first aspect, the invention relates to an occlusion device for closing an anatomical defect in tissue comprising a conduit connecting an opening on a first tissue and an opening on a second tissue. The occlusion device comprises a scaffold comprising:

a) a proximal support structure comprising at least two arms;

b) a distal support structure comprising at least two arms, wherein the arms are adapted to provide anchorage for the device in the tissue; and c) a waist portion adapted for extending through the opening on the first tissue and connecting the proximal support structure with the distal support structure, wherein the scaffold consists essentially of a biodegradable polymer, wherein the proximal support structure and the distal support structure comprise or consist of polycaprolactone (PCL), poly-(D,L-lactide-co-caprolactone) (PLC), or a mixture thereof.

In a second aspect, the invention relates to a method of closing an anatomical defect in a tissue comprising a conduit connecting an opening on a first tissue and an opening on a second tissue. The method comprising:

a) providing a sheath into which an occlusion device according to the first aspect has been inserted;

b) moving the sheath containing the occlusion device through the opening on the second tissue, the conduit, and the opening on the first tissue;

c) moving the proximal support structure of the occlusion device out of the sheath through the opening on the first tissue by using a delivering means;

d) deploying the proximal support structure at the front side of the first tissue to close the defect from the front side;

e) withdrawing the sheath to release a portion of the waist portion of the occlusion device in the opening and to release the distal support portion and the remaining portion of the waist portion in the conduit; and f) deploying the distal support structure of the occlusion device in the conduit to anchor the device.

In a third aspect, the invention relates to use of an occlusion device according to the first aspect or a method according to the second aspect for closing a septal defect or shunt in the heart or the vascular system.

BRIEF DESCRIPTION OF THE DRAWINGS

The invention will be better understood with reference to the detailed description when considered in conjunction with the non-limiting examples and the accompanying drawings, in which.

Figure 1:
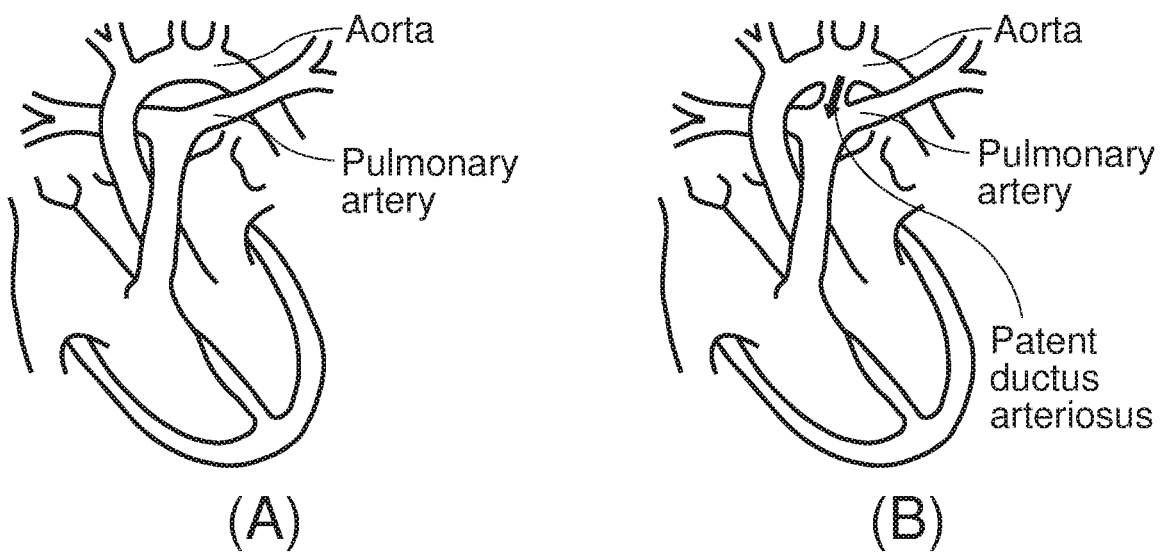
FIG. 1 is a schematic diagram showing a comparison between (A) a normal heart and (B) a heart with patent ductus arteriosus (PDA). As can be seen from FIG. 1B, the ductus arteriosus remains open, and the opening allows oxygen-rich blood from the aorta to mix with oxygen-poor blood from the pulmonary artery. This may strain the heart and increase blood pressure in the lung arteries.

In the figure, an occlusion device (500) comprising a scaffold (60) and a delivering system (100) is shown. The scaffold (60) comprises a proximal support structure (40), a distal support structure (20), and a waist portion (30). The proximal support structure (40) comprises at least two arms, in the form of a plurality of spokes (42) outwardly extending from the middle (41) of the proximal support structure (40). In the embodiment shown, a proximal occlusion film (43) is supported by the proximal support structure (40), whereby the proximal occlusion film (43) is expanded between the spokes (42) of the proximal support structure (40). The distal support structure (20) comprises at least two arms, in the form of a plurality of spokes (22) outwardly extending from the middle (21) of the distal support structure (20). The waist portion (30) connects the proximal support structure (40) with the distal support structure (20).

The delivering system (100) comprises a delivering means (101) and a sheath (103). In the embodiment shown, the delivering means (101) is in the form of a rod for removably connecting to the proximal support structure (40) or to the distal support structure (20). As depicted in the figure, the rod comprises a threaded exterior surface (104) to engage with the threaded interior surface (not shown) of the proximal support structure (40) or the distal support structure (20). The reinforced rod housing (102) act as the force support of the rod during delivery.

Figure 3:
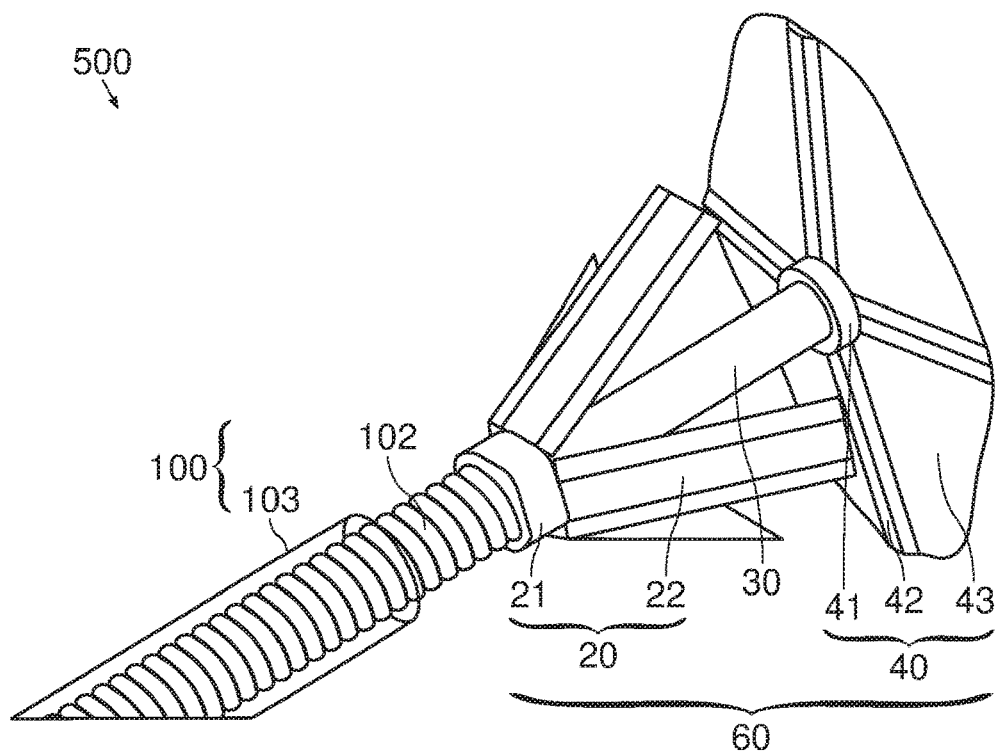

FIG. 3 shows a perspective view of an occlusion device according to an embodiment of the invention in an assembled state.

The delivering means (not shown) is connected to the scaffold (60), which may take place via the proximal support structure (40) or the distal support structure (20).

Figure 4:
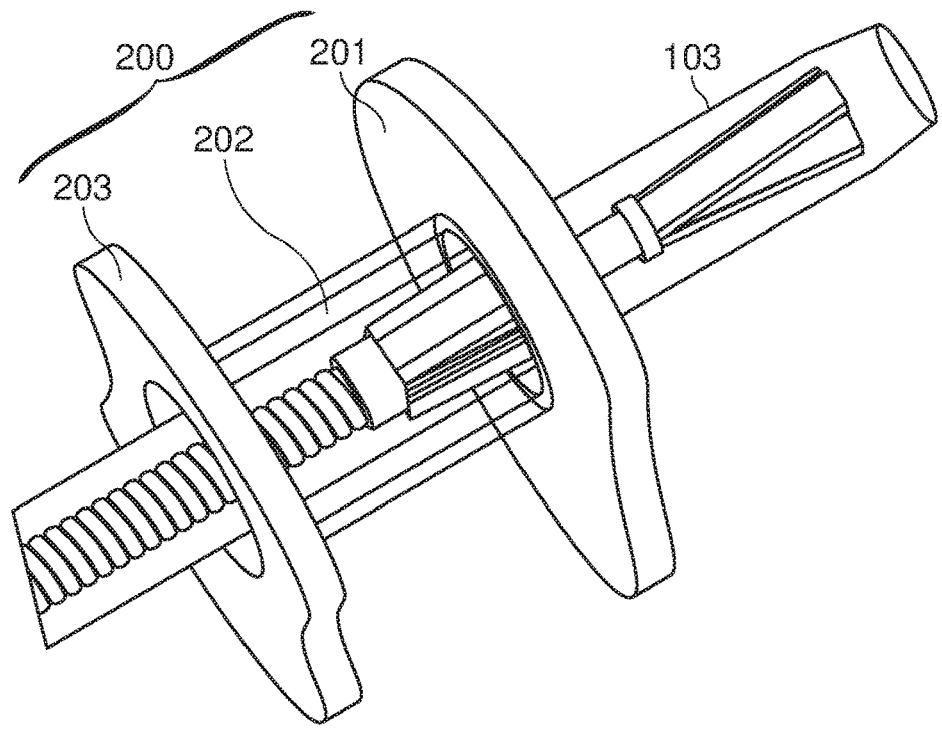

FIG. 4 shows a perspective view of an occlusion device according to an embodiment of the invention in a mode of use.

In the figure, (200) denotes a patent ductus arteriosus (PDA) condition, whereby (201) denotes the aorta wall, (203) denotes the pulmonary artery wall, and (202) denotes the conduit between the aorta and the pulmonary artery wall. As seen from the figure, the sheath (103) is moved through the opening on the pulmonary artery wall (203) ("second tissue"), the conduit (202), and the aorta wall (201) ("first tissue"). The occlusion device is inserted into the sheath (103).

Figure 5:
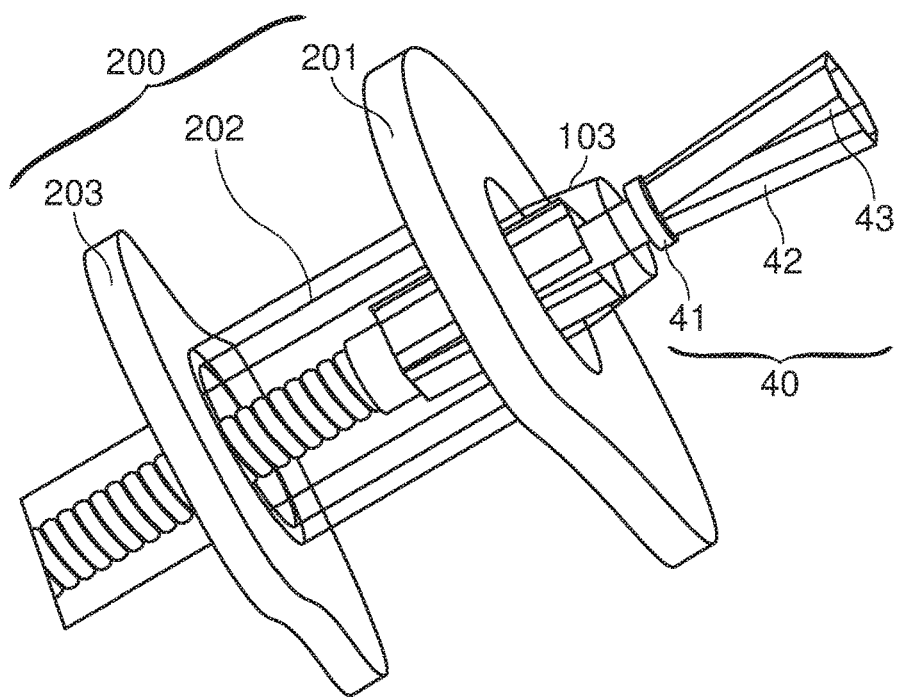

FIG. 5 shows a perspective view of an occlusion device according to an embodiment of the invention in a mode of use. In the figure, the proximal support structure (40) of the occlusion device is moved out of the sheath (103) through the opening on the aorta wall (201).

Figure 6:
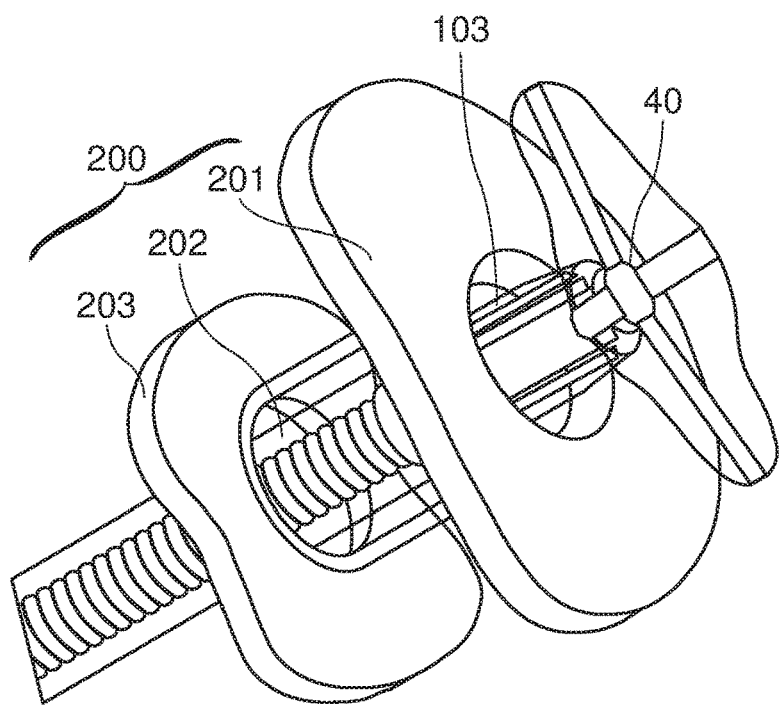

FIG. 6 shows a perspective view of an occlusion device according to an embodiment of the invention in a mode of use. In the figure, the proximal support structure (40) is deployed at the front side of the aorta wall (201).

Figure 7:
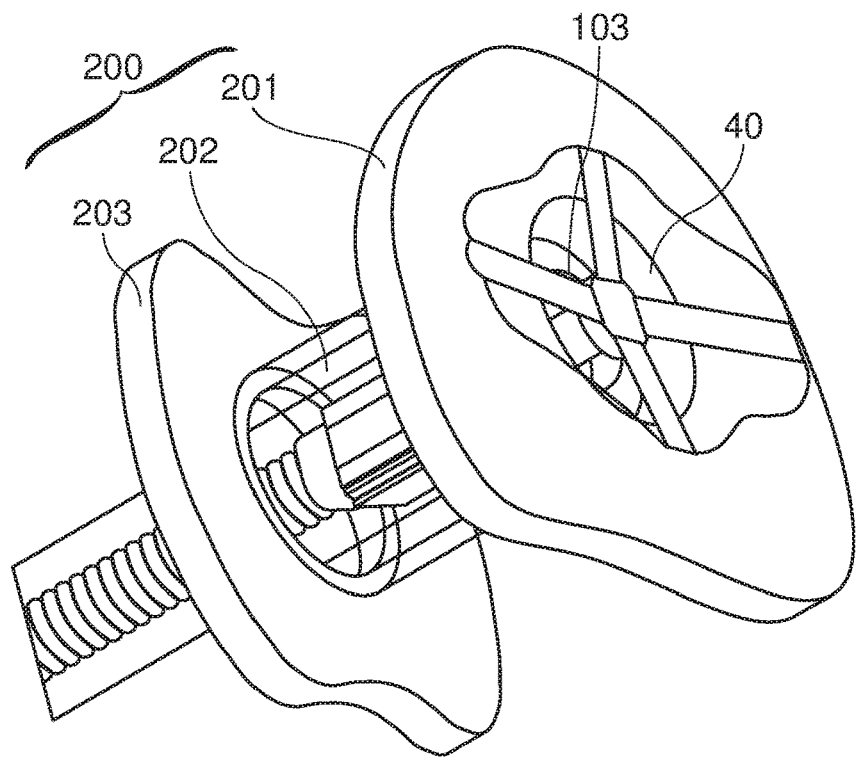

FIG. 7 shows a perspective view of an occlusion device according to an embodiment of the invention in a mode of use. In the figure, the proximal support structure (40) is deployed at the front side of the aorta wall (201), and the position of the proximal support structure (40) is adjusted such that the defect is closed from the front side of the aorta wall (201) by the proximal occlusion film.

Figure 8:
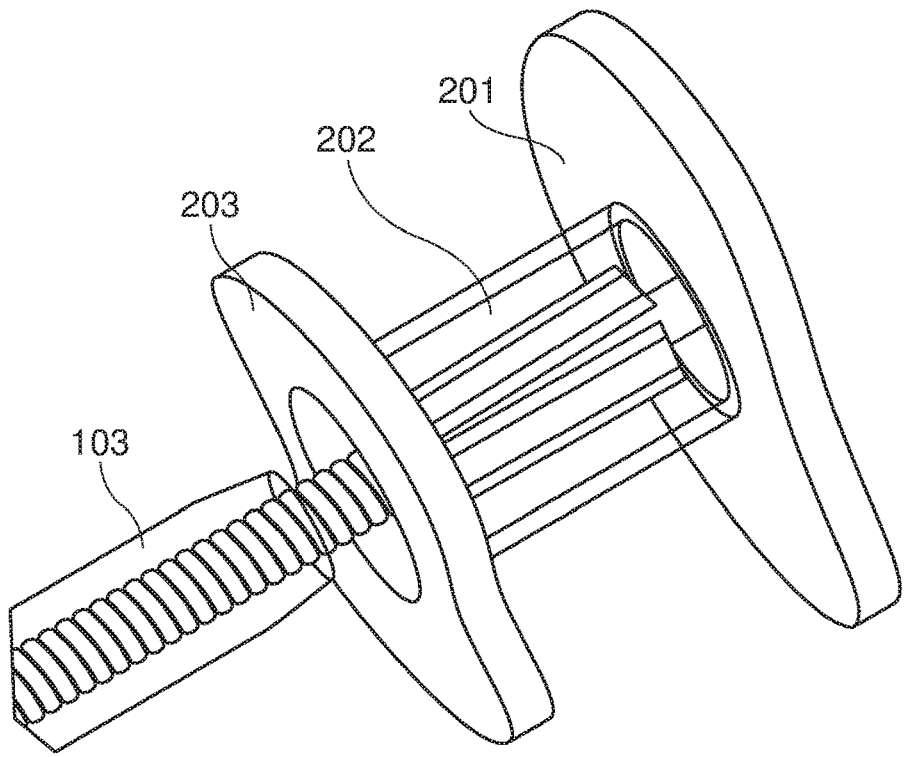

FIG. 8 shows a perspective view of an occlusion device according to an embodiment of the invention in a mode of use. After the proximal support structure is deployed to close the defect, the sheath (103) is withdrawn to release a portion of the waist portion of the occlusion device in the opening, and to release the distal support portion and the remaining portion of the waist portion in the conduit (202).

Figure 9:
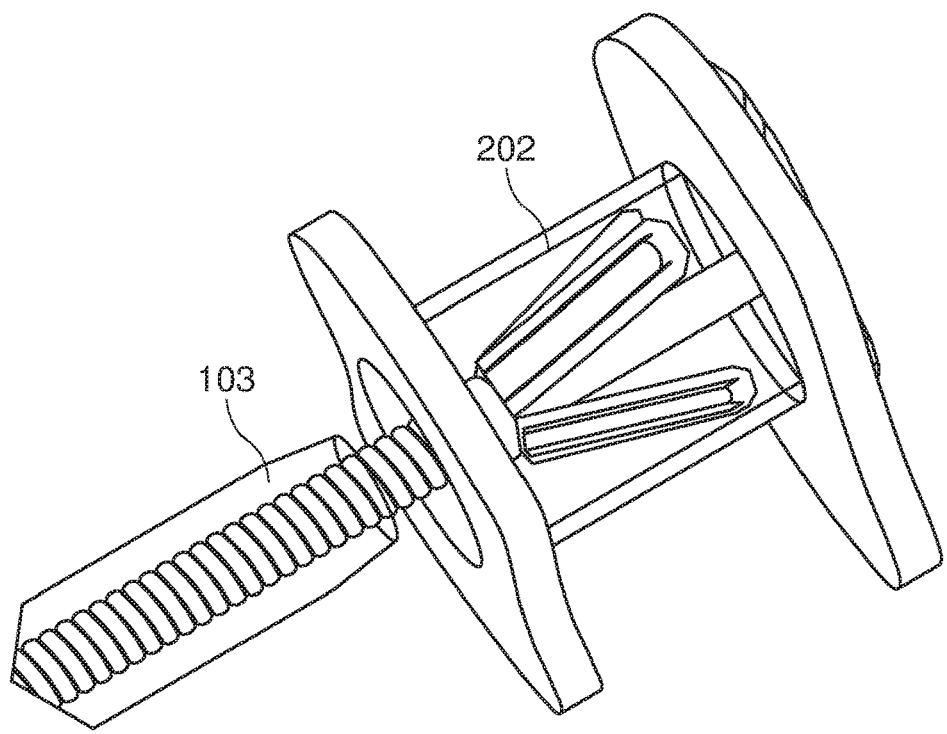
Figure 10:
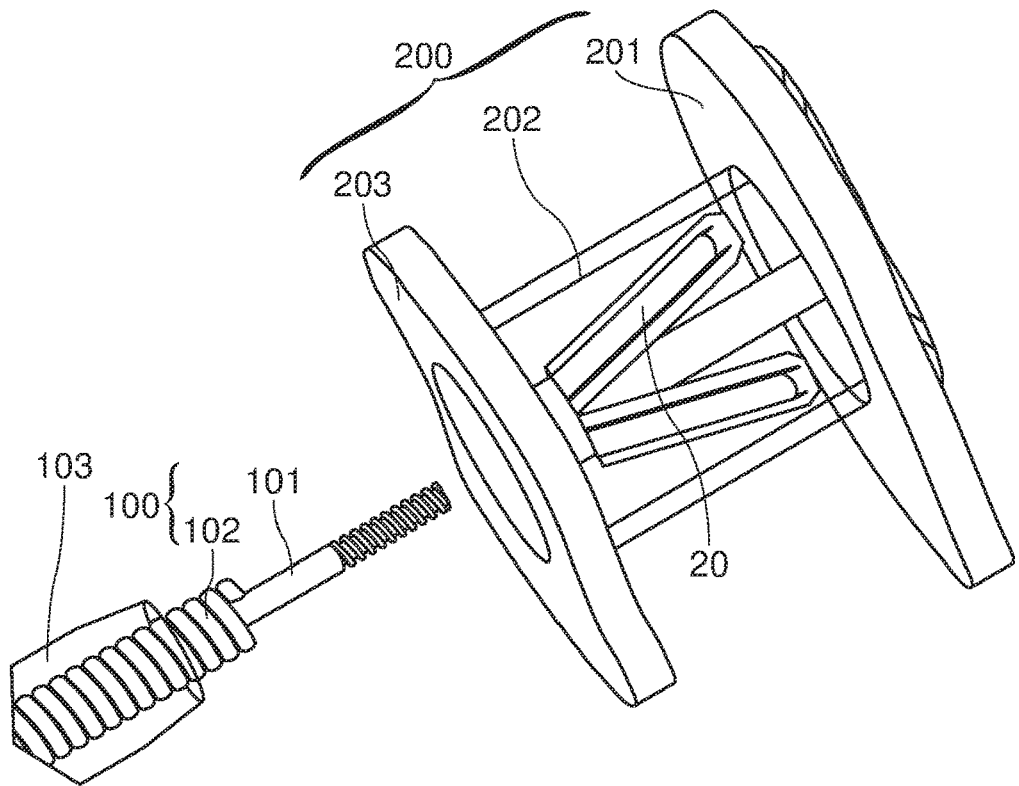

FIG. 9 shows a perspective view of an occlusion device according to an embodiment of the invention in a mode of use. The distal support structure of the occlusion device is deployed in the conduit (202) to anchor the device FIG. 10 shows a perspective view of an occlusion device according to an embodiment of the invention in a mode of use. The delivering means (101) is disconnected from the proximal support structure (40) or the distal support structure (20), and is moved out of the conduit (202).

Figure 11:
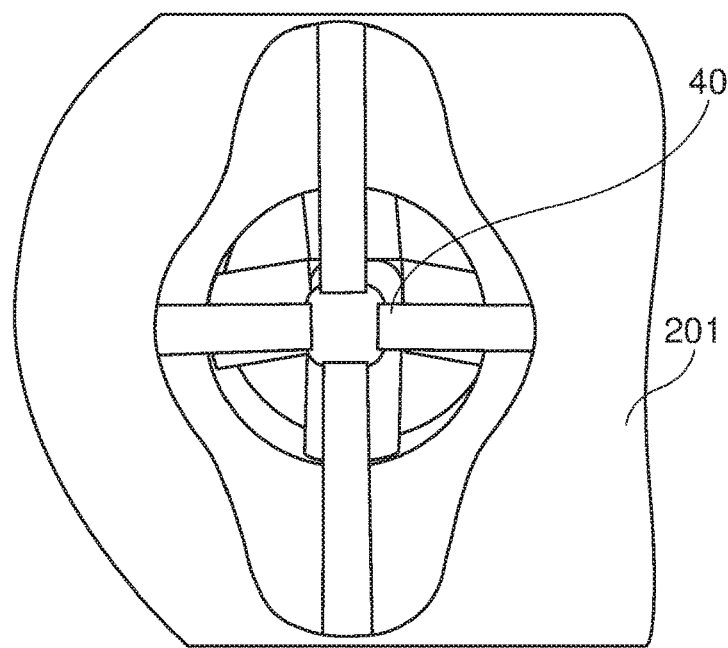

FIG. 11 shows the view of the occlusion device at PDA looking from the front side of the aorta wall (201).

Figure 12:
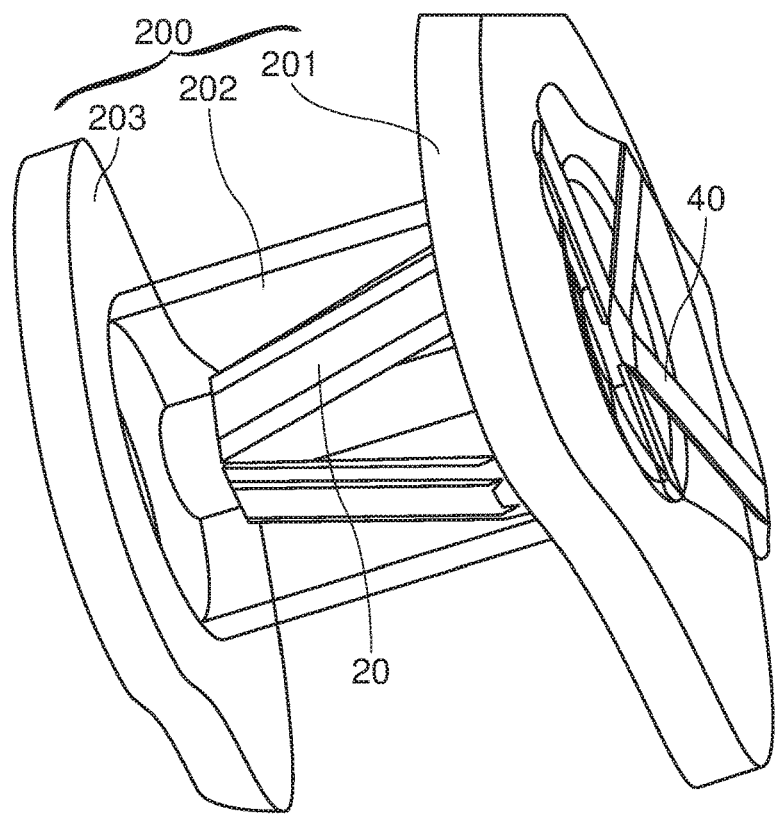

FIG. 12 shows the side view of an occlusion device according to an embodiment of the invention in a mode of use, when engaged at the PDA defect. As can be seen from the figure, the arms of the deployed distal support structure outwardly extends from the middle of the distal support structure (20) and contacts the wall of the conduit (202), thereby anchoring the device in the tissue.

Figure 13:
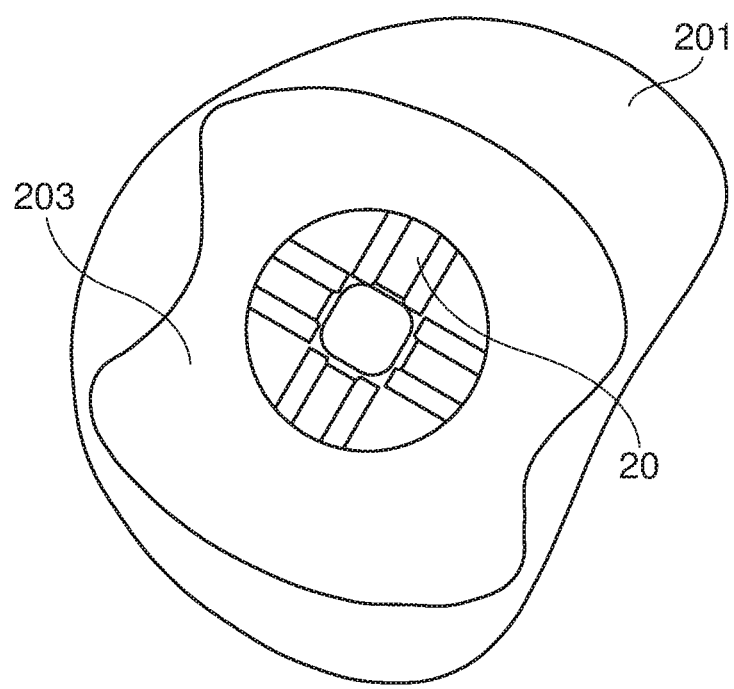

FIG. 13 shows the view of the occlusion device at PDA looking from the side of the pulmonary artery wall (203).

Figure 14:
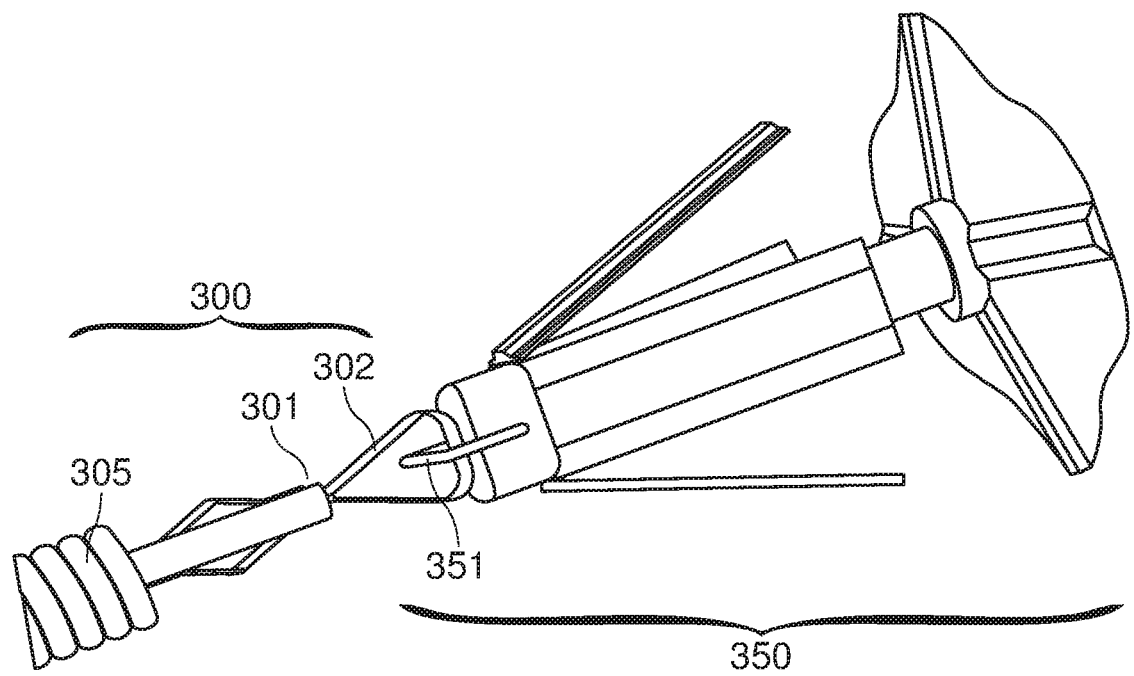

FIG. 14 shows a perspective view of an occlusion device according to another embodiment of the invention in an assembled state. A loop (351) is attached to the scaffold (350) via the distal support structure of the scaffold. The delivering means (301) is in the form of a rod (305) comprising a forceps (302) to removably engage with the loop (351).

Figure 15:
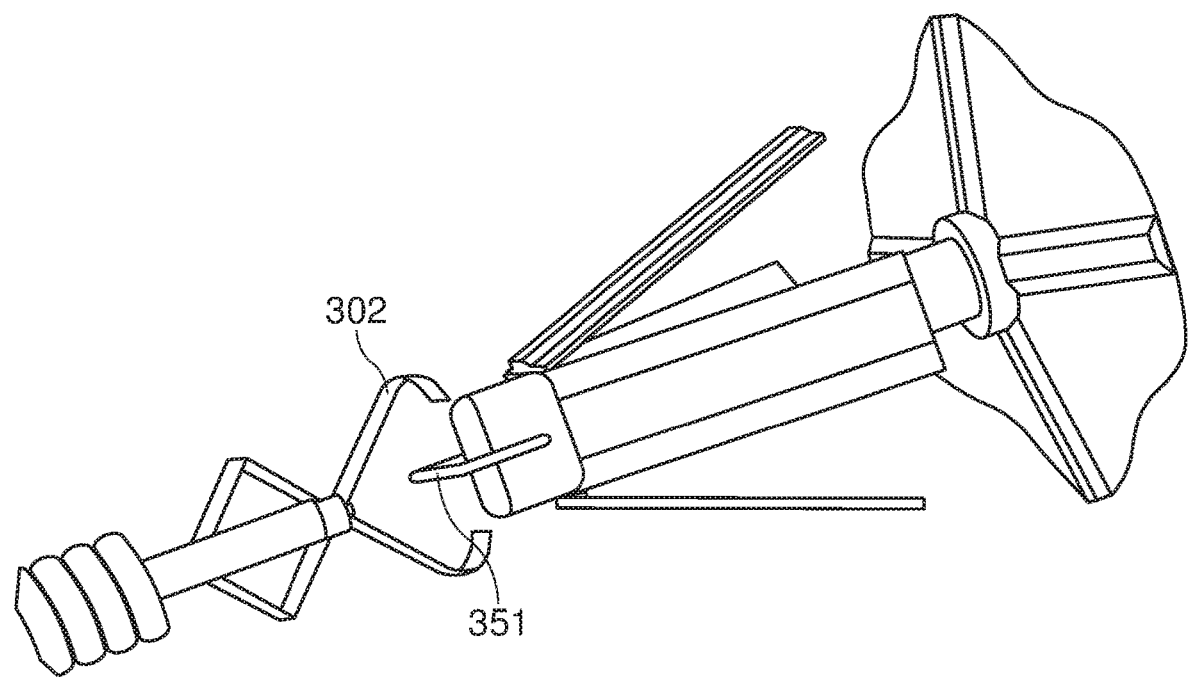

FIG. 15 shows a perspective view of an occlusion device according to another embodiment of the invention in an unassembled state. The forceps (302) is disengaged with the loop (351), thereby disconnecting the delivering means from the scaffold.

DETAILED DESCRIPTION OF THE INVENTION

In a first aspect, the present invention refers to an occlusion device for closing an anatomical defect in tissue comprising a conduit connecting an opening on a first tissue and an opening on a second tissue.

In the context of the present invention, an occlusion device is a catheter-deliverable device that closes a hole in the wall of a tissue like a hole or opening in the septa of a heart. In various embodiments, the occlusion device is used to close a hole in an aorta wall for treating patent ductus arteriosus. Once in place, the occlusion device is released on both sides of the defect from the sheath. A proximal occlusion film may be supported by the proximal support structure, which closes the defect when the proximal support structure is deployed. The deployed occlusion device is kept in place by pressure of the deployed distal support structure against the sides of the conduit. The occlusion device thus may function as a permanent implant that stays in the body after the procedure. The occlusion device may, however, also be used in in vitro methods for closing tissue defects outside the body, for example.

The occlusion device comprises a scaffold, the scaffold comprising a proximal support structure comprising at least two arms; a distal support structure comprising at least two arms, wherein the arms are adapted to provide anchorage for the device in the tissue; and a waist portion adapted for extending through the opening on the first tissue and connecting the proximal support structure with the distal support structure. The term "proximal", also referred herein as "tail end" or "tail" of the occlusion device, refers to a location that in use is closest to the opening that is to be closed by the device. The term "distal", also referred herein as "head end" or "head" of the occlusion device, on the other hand, refers to a location furthest from the opening that is to be closed by the device.

The scaffold may further comprise occlusion films. In this embodiment, the arms of the proximal support structure may support a proximal occlusion film. Even though the arms of the distal support structure may also support a distal occlusion film, a distal occlusion film is not required, and is generally not used in the occlusion device of the first aspect. Advantageously, an anatomical defect in tissue may be closed by an occlusion device of the first aspect without the use of an occlusion film, or with only a proximal occlusion film.

The scaffold of the occlusion device consists essentially of a biodegradable polymer. In various embodiments, the proximal support structure, the distal support structure, the waist portion, and the proximal occlusion film consist essentially of a biodegradable polymer.

The terms "bioabsorbable", "biodegradable" and "bioresorbable" are used interchangeably herein, and refers to the ability of a material to degrade or breakdown over a period of time due to the chemical and/or biological action of the body. In the context of the present invention, the term "biodegradable polymer" refers to a polymer comprising one or more polymeric components that can be completely removed from a localized area by physiological metabolic processes such as resorption. For example, a biodegradable polymer may, when taken up by a cell, be broken down into smaller, non-polymeric subunits by cellular machinery, such as lysosomes or by hydrolysis that the cells can either reuse or dispose of without significant toxic effect on the cells. Examples of biodegradation processes include enzymatic and non-enzymatic hydrolysis, oxidation and reduction. Suitable conditions for non-enzymatic hydrolysis, for example, include exposure of biodegradable material to water at a temperature and a pH of a lysosome (i.e. the intracellular organelle). The degradation fragments typically induce no or little organ or cell overload or pathological processes caused by such overload or other adverse effects in vivo.

Various examples of biodegradable polymer materials are known in the art, any of which are generally suitable for use as the biodegradable polymer of the present invention. Examples of polymers that are considered to be biodegradable include aliphatic polyesters, poly(amino acids), copoly (ether-esters), polyalkylenes oxalates, polyamides, poly (iminocarbonates), polyorthoesters, polyoxaesters, polyamidoesters, polyoxaesters containing amido groups, poly(anhydrides), polyphosphazenes, polycarbonates, naturally-occurring biodegradable polymers such as chitosan, collagen, starch, and blends thereof. Examples of polyortho esters include a polylactide, a polyglycolide, a polycaprolactone, a polylactic acid, a biodegradable polyamide, a biodegradable aliphatic polyester, and/or copolymers thereof, or with other biodegradable polymers such as those mentioned above.

Most bioabsorbable polymers available today, such as polylactic acids (PLA), polycaprolactone (PCL) and polylactic-co-glycolic acid (PLGA) display a very similar mechanical behavior, with a high Young's modulus and rather low elongation at break values. Sometimes these polymers seem in a pure form inappropriate for this clinical application where highly flexible biodegradable materials are required because of the huge expansion ratio before and after deployment. One of the most practical strategies for tuning the properties of polymers is blending with another polymer or copolymerization. Copolymerization facilitates a broad range of properties, including good mechanical strength, biocompatibility, biodegradability, and processability, which makes them excellent materials for medical application.

In various embodiments, the biodegradable polymer is polycaprolactone (PCL), poly-(D,L-lactide-co-caprolactone) (PLC), poly-L-lactide (PLLA), poly-D-lactide (PDLA), polyglycolide (PGA), polylactic acid (PLA), polycaprolactone-polylactic acid copolymer (PCL-PLA copolymer), polylactide-polyglycolide copolymer (PLGA), poly (trimethylene carbonate) (TMC); copolymers of polycaprolactone (PCL) and poly(trimethylene carbonate) (TMC); triblock copolymers of polylactic acid (PLA), polycaprolactone (PCL) and/or poly(trimethylene carbonate) (TMC); polylactic acid-polyethylene oxide copolymers, polygluconate polyhydroxybutyrate, polyanhydride, polyphosphoester, poly(amino acids), polydioxanone, cellulose, collagen, chitosan, or a mixture thereof.

Biodegradable polymers that are particularly suitable for use to form the waist portion of the occlusion device of the invention include polycaprolactone (PCL), poly-(D,L-lactide-co-caprolactone) (PLC), poly-L-lactide (PLLA), poly-D-lactide (PDLA), polyglycolide (PGA), polylactic acid (PLA), polycaprolactone-polylactic acid copolymer (PCL-PLA copolymer), polylactide-polyglycolide copolymer (PLGA), poly(trimethylene carbonate) (TMC); copolymers of polycaprolactone (PCL) and poly(trimethylene carbonate) (TMC); triblock copolymers of polylactic acid (PLA), polycaprolactone (PCL) and/or poly(trimethylene carbonate) (TMC), or a mixture thereof. In various embodiments, the waist portion comprises a biodegradable polymer as listed above. In various embodiments, the waist portion consists essentially of the biodegradable polymer.

The proximal support structure and the distal support structure comprised in the occlusion device comprise polycaprolactone (PCL), poly-(D,L-lactide-co-caprolactone) (PLC), or a mixture thereof. In various embodiments, the proximal support structure and the distal support structure comprised in the occlusion device consist of polycaprolactone (PCL), poly-(D,L-lactide-co-caprolactone) (PLC), or a mixture thereof. Polycaprolactone (PCL), poly-(D,L-lactide-co-caprolactone) (PLC), or their mixture are particularly suited to form the proximal support structure and the distal support structure due to their mechanical attributes such as flexibility and stiffness. Poly(D,L-lactide-co-caprolactone) (PLC) refers to a copolymer of poly(D,L-lactide) and poly(caprolactone), where the appropriate weight ratio of poly(D,L-lactide) to poly(caprolactone) in the copolymer may be in the range of about 1:1 to about 9:1, such as about 2:1, about 3:2, or about 7:3. In one embodiment, the weight ratio of poly(D,L-lactide) and poly(caprolactone) in the copolymer is about 7:3.

The proximal support structure or the distal support structure, or both support structures may independently from each other, comprise three or more spokes outwardly extending from the middle of the proximal support structure as the at least two arms. The spokes may be connected at their inner ends with each other so that they are arranged like spokes in a wheel or an umbrella. Alternatively, the spokes may be connected to a middle section, for example a joint section. In both cases, the support structure may be foldable and may, thus, be adapted to be folded at their inner ends of the arms to be insertable into a sheath. Thereby, the arms may be folded inwardly or outwardly, i.e. in the direction of the waist portion or away from the waist portion. In various embodiments, the arms of the proximal support structure folds outwardly away from the waist portion.

The arms of the distal support structure may be adapted to provide anchorage for the device in the tissue by outwardly extending from the middle of the distal support structure and contacting the conduit wall. In so doing, upon deployment of the distal support structure in the conduit, pressure exerted by the distal support structure on the conduit walls serves to keep the scaffold in place. In various embodiments, the arms of the distal support structure folds inwardly in the direction of the waist portion, such that when the distal support structure is deployed, the arms of the distal support structure outwardly extend and contact the conduit wall to act as an anchor for the occlusion device. The arms of the distal support structure may also fold outwardly away from the direction of the waist portion, such that when the distal support structure is deployed, the arms of the distal support structure outwardly extend and contact the conduit wall to act as an anchor for the occlusion device. In both configurations, the distal support structure of the scaffold is at least substantially contained within, or is contained in its entirety within the conduit. In embodiments wherein the conduit is ductus arteriosus, for example, the distal support structure of the scaffold may be contained in its entirety within the ductus arteriosus such that the scaffold does not extend into the pulmonary artery. As such, hemodynamic flow in the pulmonary artery is not obstructed.

As an alternative, a joint section may be integrally provided together with the arms or spokes of the support structure, but can then be folded. Therefore, in one embodiment this part of the support structure is adapted to resist high mechanical stress.

The number of arms is not limited as long as the support structure can close the defect. For example, in case the proximal support structure comprises an occlusion film, the number of arms can include 2 or more arms as long as the proximal support structure can support a proximal occlusion film. The proximal and/or the distal support structures may include, but are not limited to 2 to 8 arms or spokes, such as 2, 3, 4, 5, 6, 7, or 8 arms or spokes. The number of spokes in the proximal support structure and in the distal support structure may be the same or different. In various embodiments, the number of arms of the proximal and the distal support structure is the same, and contains three arms each.

The form of the arms or spokes is generally like a rod having a rounded or any other cross section, such as square, rectangular, hexagonal, octagonal or triangular. Rounded means in the context of the present application, that the supporting means can have a circular cross section or an oval cross section. The edging of the arms or spokes can be rounded.

In another embodiment, the outwardly extending arms of the proximal support structure are spokes forming together with the occlusion film, a disk-shaped occlusion structure. Disk-shaped means in the context of this application that the shape is like a circular disk, but can also be curved like a shell. Thus, the disc-shaped occlusion structure may be in any form between a disk and a half-shell. If the support structure and the occlusion film are in a half-shell, they look like an umbrella when connected to the longitudinal waist portion.

In this regard, the proximal occlusion film may, in the context of the present application, be connected to the proximal support structure, for example, by welding the film on the support structure. As an alternative to the welding of the film, the film may be glued, laminated or sewed to the support structure. In general one or more films may be used as the proximal occlusion film. For example, two, three, or four films may be provided on the proximal support structure in a laminated structure.

In a particular embodiment of the first aspect, the proximal support structure may be formed together with the proximal occlusion film by hot pressing in one or two consecutive steps. In one step, the supporting means are formed of the same material as the film, but having a higher thickness. Thereby, an integrally formed proximal occlusion disc comprising the proximal support structure and the proximal occlusion film can be easily formed.

The proximal occlusion film, which is supported by the proximal support structure, may be adapted to be disposed together with the proximal support structure at the front side of the defect in the first tissue.

In a further embodiment, the proximal occlusion film may extend between the arms of the proximal support structure. The term "extend" in the context of the present application means that the film extends from one arm to the proximate arm and can be spanned between the arms or spokes. Alternatively, the proximal occlusion film may be spanned over the supporting means of the proximal support structure, thereby forming the disk-shaped structure for closing the defect from the front side of the first tissue.

The size and the form of the film section may be freely adjusted depending on the size of the defect to be closed. In addition, the dimensions of the proximal portion of the occlusion device may be adjusted so that the device may be placed in and pushed through a catheter sheath and has a working size (diameter) of the film portion in the working structure which is sufficient for closing the opening, for example in the septum or in the aorta wall. Such a transcatheter-closeable defect usually has a diameter of up to 40 mm. The diameters of the occlusion devices, i.e. the diameter of the proximal occlusion films may be about 70 mm, 60 mm, 50, mm, 40 mm, 30 mm, 20 mm, or may be provided in a size range of about 12 to 16 mm. In one example, the proximal occlusion film has a diameter of about 12 mm. The diameter depends on the size of the defect to be sealed. The size of the film, i.e. the proximal disk-shaped structure, should be adapted such that a defect may be sufficiently closed. The term "sufficiently closed" in the context of the present invention is used to describe the condition that after insertion of the occlusion device into an opening, the liquid flow from the back side to the front side and the liquid flow from the front side to the back side of the closed opening can no longer be observed, for example by echocardiography or any other method used in the art to measure the liquid flow through an opening.

The thickness of the occlusion films (if present) of the occlusion device may be at least about 10, 20, 30, 40, 50, 60, 70, 80, 90, 100, 110, 120 µm but below 500, 450, 400, 350, 300, 250, 200, 190, 180, 170, 160, 150 µm as long as the material has a suitable flexibility to be folded into the sheath during the deployment procedure.

The proximal support structure and/or the distal support structure may comprise a connector adapted for connecting the respective support structure with the waist portion. The connector may, for example, be a joint protruding in the middle of the proximal and/or distal support structure in the direction of the waist portion.

In one embodiment, the waist portion may be a tube, such as a polymeric tube, like a stem adapted to receive the joint of the proximal support structure from its proximal end and to receive the joint of the distal support structure from its distal end. Thus, the proximal support structure and the distal support structure may be connected by joint connection to the waist portion, respectively. The joints of the support structures may be adapted to be inserted into the waist portion, such as being inserted into the tube with the end of the joint not connected to the arm or spoke.

The waist portion may be formed to extend through the opening of the defect or the opening on the first tissue, and may thus be adapted to the tissue thickness at the opening or may be elastic enough to accommodate different opening thicknesses. The elasticity may be adjusted by common methods such as the material elasticity, the material thickness, the wall thickness of the tube, and the like. The waist portion may have a length of between about 1 and 10 mm, for example, about 1, 2, 3, 4, 5, 6, 7, 8, 9, or 10 mm. The waist portion may be a tube having a diameter of about 0.5 to 2.0 mm, for example, about 0.5, 0.6, 0.7, 0.8, 0.9, 1.0, 1.1, 1.2, 1.3, 1.4, 1.5, 1.6, 1.7, 1.8, 1.9, or 2.0 mm. The wall thickness of the tube, if the waist portion is in the form of a tube, may be between about 0.05 and 0.50 mm, for example, about 0.05, 0.06, 0.07, 0.09, 0.11, 0.13, 0.15, 0.17, 0.19, 0.21, 0.23, 0.25, 0.27, 0.29, 0.30, 0.35, 0.40, 0.45 or 0.50 mm. In alternative embodiments of this aspect, the waist portion may be a solid stem which is glued, welded or connected in a similar manner at the respective support structure.

In various embodiments, the proximal support structure, the distal support structure and the waist portion of the scaffold are integrally formed. This may be suitable for embodiments in which the scaffold is formed from the same polymeric material, where polymer processing methods such as cast molding, injection molding and compression molding may be used to form the scaffold. In alternative embodiments, it may be suitable to prepare separate parts of the device from different polymeric materials to specifically adjust the required performance of the material. For instance, the proximal support structure may be made more flexible than the remainder of the scaffold. Using different polymeric materials may also serve to alter the biodegradability of different portions of the occlusion device to result in a sequential degradation of different parts of the occlusion device. It is also possible to form all parts of the device from the same material but having specific thicknesses such that each part has the flexibility of stiffness required for its function. For example, in one embodiment the support structures or the waist portion can be stiffer than the film portions of the device by adjusting the thickness of the various parts.

In various embodiments, the proximal support structure has shape memory. The term "shape memory" generally refers to the ability of a material to remember a particular shape, such that, after being forced into another shape by application of an applied force, it assumes or returns to its original shape when the applied force is removed. In the present context, the proximal support structure of the occlusion device may elastically deform in response to an applied force, and returns to more than 50% of its original shape upon release of the applied force.

By forming the scaffold from essentially biodegradable materials, the device may, for example, be absorbed by the body within short time of a few years to several months, such as 24, 20, 18, 16, 14, 12, 10, 9, 8, 7, 6, 5, 4, 3 or 2 months.

For adjusting the performance of the polymers, plasticizers may be used. In the context of the present invention, "plasticizer" generally means a substance added to a polymer material to soften it and to improve flexibility. More particularly, the plasticizer which may be used in the occlusion device of the first aspect may preferably lower the glass transition temperature, Tg, the modulus, i.e. increases the elongation at break, or change the crystalline behavior of a polymer material or can adjust the melting temperature, Tm. Any known plasticizer may be used in the polymeric material as long as the plasticizer provides the polymer with the above-mentioned properties. The plasticizer may also be biocompatible, especially non-toxic. However, due to the small amount of plasticizer used compared to the entire body mass of a patient, use of a plasticizer that may have some adverse effects on the human body is also within the scope of the invention.

Some illustrative examples of plasticizer that can be used in the present invention include, but are not limited to triethyl citrate (TEC), polyalkylene glycols such as polyethylene glycols (PEG) or polypropylene glycols, propylene glycol (PG) glycerol, di-2-ethylhexyladipate (dioctyladipate), di-2-ethylhexylphthalate (dioctylphthalate), dicyclohexylphthalate; diisononyladipate; diisononylphthlate; n-butyl benzyl phthalate, 1,3-butylene glycol/adipic acid polyester (1700-2200 MW) containing 16 weight percent terminal myristic, palmitic and stearic acid ester functionality. Other examples of plasticizers include epoxidized butyl esters of linseed oil fatty acid, epoxidized linseed oil or epoxidized soya oil. Examples of polyalkylene glycols include low molecular weight (MW) compounds having an MW of about 60-about 8000, or about 100-6000, about 100-5000, about 100-4000, or about 150-2000. Illustrative examples include diethylene glycol, triethylene glycol, dipropylene glycol, or tripropylene glycol, too name only a few. The amount of plasticizer is not limited but is generally adjusted such that the biodegradable polymer material maintains mechanical integrity during its use, including for example, during the storage and upon deployment. In some embodiments of the invention, the plasticizer may be contained in one or all of the polymer materials in an amount of about 1 to about 30 wt %, or about 1-25 wt %, about 2-25 wt %, about 3-25 wt %, about 4-25 wt %, about 5-25 wt %, about 6-25 wt %, about 2-20 wt %, about 3-20 wt %, about 4-20 wt %, or about 5-20 wt %, based on the dry weight of the polymer material. In line with the above, the amount of plasticizers can for example be about 1, 2, 3, 4, 5, 6, 7, 8, 9, 10, 12, 15, 17, 19, 21, 23, 25, 27, or 29 wt %, based on dry weight of the respective polymer material.

In an alternative embodiment of the occlusion device of the first aspect, one or more elements selected from the proximal support structure, the proximal occlusion film, the distal support structure, and the waist portion may be made of a material comprising a therapeutically active agent.

In the context of the present invention, the term "therapeutically active agent" generally means a therapeutic or pharmaceutical agent which may be mixed into the polymer composition, or impregnated or incorporated into the scaffold. In various embodiments, the therapeutic active agent is present as a coating on the proximal occlusion film.

The therapeutic agent may be any therapeutic or pharmaceutical agent suitable for use in drug-containing materials for occlusion devices. Various examples include, but are not limited to antiproliferative/antimitotic agents including natural products, such as vinca alkaloids (e.g. vinblastine, vincristine, and vinorelbine), paclitaxel, epidipodophyllotoxins (e.g. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiproliferative/antimitotic alkylating agents such as nitrogen mustards (such as mechlorethamine, cyclophosphamide and analogs, melphalan, chlorambucil), ethylenimines and methylmelamines (hexamethylmelamine and thiotepa), alkyl sulfonates-busulfan, nirosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (e.g. estrogen); anticoagulants (heparin, synthetic heparin salts and other inhibitors of thrombin); fibrinolytic agents (such as tissue plasminogen activator, streptokinase and urokinase); antiplatelet (such as aspirin, dipyridamole, ticlopidine, clopidogrel, abciximab); antimigratory; antisecretory (such as breveldin); antiinflammatory: such as adrenocortical steroids (cortisol, cortisone, fludrocortisone, prednisone, prednisolone, 6-alpha-methylprednisolone, triamcinolone, betamethasone, and dexamethasone), non-steroidal agents (such as salicylic acid derivatives e.g. aspirin); para-aminophenol derivatives (e.g. acetaminophen); indole and indene acetic acids (such as indomethacin, sulindac, and etodalac), heteroaryl acetic acids (such as tolmetin, diclofenac, and ketorolac), arylpropionic acids (such as ibuprofen and derivatives), anthranilic acids (such as mefenamic acid, and meclofenamic acid), enolic acids (such as piroxicam, tenoxicam, phenylbutazone, and oxyphenthatrazone), nabumetone, gold compounds (such as auranofin, aurothioglucose, gold sodium thiomalate); immunosuppressive (such as cyclosporine, tacrolimus (FK-506), sirolimus (rapamycin), azathioprine, mycophenolate mofetil); angiogenic such as vascular endothelial growth factor (VEGF), fibroblast growth factor (FGF); nitric oxide donors; antisense oligo nucleotides and combinations thereof.

The therapeutic agent may particularly include, but is not limited to, a drug, an antibiotic, an anti-inflammatory agent, an anti-clotting factor, a hormone, a nucleic acid, a peptide, a cellular factor, a growth factor, a ligand for a cell surface receptor, an anti-proliferation agent, an anti-thrombotic agent, an antimicrobial agent, an anti-viral agent, a chemotherapeutic agent, or an anti-hypertensive agent to improve the sealing effect, the healing process, or preventing thrombi, for example.

In this context, it is noted that the therapeutically active agent to be incorporated into one or more polymeric materials of the occlusion device may be a drug, a protein, a growth factor, or combinations thereof.

In the context of the invention, the term "drug" generally means a therapeutic or pharmaceutical agent which may be included/mixed into the biodegradable polymer, impregnated, dispersed within or dissolved into the biodegradable polymer in order to provide a drug-eluting composition. The term "protein" is meant any naturally occurring polypeptide that comprises more than 40 amino acid residues. The protein may be a full length protein or a truncated form, for example, an active fragment. Illustrative examples of proteins include, but are not limited to antibodies or other binding proteins with antibody like properties (for example, affibodies or lipocalin muteins knows as "Anticalins®") for selected cell receptors, growth factors such as VEGF (Vascular Endothelial Growth Factor) and similar factors for transmitting signals, cardiovascular therapeutic proteins or cardiac hormones and active fragments thereof or prohormones or preprohormones of such cardiac hormones (these hormones or the prohormones can either be peptides as defined herein, if they have less than 40 amino acid residues of a protein, should there polypeptide sequence contain more the 40 amino acid residues). Further examples for cardiovascular therapeutic agents can be peptides or DNA such as the DNA for nitric oxide. Examples of nucleic acid molecules include sense or anti-sense DNA molecules (if expression of a target gene is to be controlled) or the coding sequence (either alone or in gene-therapy vector, for example) of a therapeutically active protein that is to be produced. In such a case, the nucleic acid may code for a protein that promotes wound healing as described in International patent application WO 97/47254, for example.

The therapeutically active agent may be dispersed within or dissolved in the biodegradable polymer used to form the occlusion device of the first aspect. For example, the drug may be present as particles within a polymeric matrix formed from the biodegradable polymer. In other embodiments, the drug may first be dissolved in the polymeric blend, prior to use of the polymeric blend to form the occlusion device. In various embodiments, the drug is homogeneously dispersed within or dissolved in the biodegradable polymer, such that drug elution from the occlusion device is at least substantially uniform. The release of the drug from the occlusion device may also be accomplished by controlled degradation of the biodegradable polymer. After drug elution, the biodegradable polymer may be biodegraded within the body in order to avoid any deleterious effects generally associated with decomposition reactions of polymer compounds in vivo.

All therapeutically active agents mentioned above can be used alone or in any combination thereof in the polymer material of this embodiment of the invention. The amount of the therapeutically active agent (or 2 or more agents together) in the polymeric material is not limited and can be as high as wanted as long as the physical properties of the polymer material, especially the glass transition temperature and the melting temperature, are not adversely affected. In some embodiments, the amount of the therapeutically active agent, based on the dry weight of the polymer material that contains the agent, may be up to about 35 wt %. The therapeutically active agent may be present in an amount of 0.1 to 35 wt %, 1 to 35 wt % or 1 to 10, 15, 20, 25 or 30 wt % based on the dry weight of the polymer material that contains the drug. In this context, it is again noted that it is possible to include more than one therapeutically active agent of the same or different type into a polymer material of the films or the supports, for example, an anti-restenotic drug and an anti-inflammatory drug or two anti-thrombotic drugs.

In various embodiments, the protein is elastin, collagen, fibronectin, laminin, or a mixture thereof. The growth factors that may be used include basic fibroblast growth factor, platelet-derived growth factor, or a mixture thereof. In various embodiments, the surface of the proximal occlusion film and/or the proximal support structure is modified by treatment with plasma, and/or a coating to facilitate closure of PDA. Such surface modification may be applied to promote occlusion of the conduit and endothelial growth while minimizing thombosis and embolization at the aorta side.

In a further embodiment of the occlusion device one or more elements selected from the group of the proximal support structure, the distal support structure, the waist portion, and the proximal occlusion film, may comprise a radiopacifier deposited at its surface and/or blended in the material the elements comprise. For example, the radiopacifier may be present in the proximal and distal support structures of the occlusion device.

The radiopacifier may for example be a material including metals, metal oxides or metal salts, such as gold particles, bariums salts or bismuth glasses, for example, but are not limited to these examples. In the present embodiment, the radiopacifier may comprise or consists of barium sulfate ($BaSO_4$). In the films, the radiopacifier may be incorporated into the polymeric material by solution casting or extruder mixing in an amount of more than 0.1, 0.2, 0.3, 0.4, 0.5, 1.0, 1.5, 2.0, 2.5, 3.0, 3.5, 4.0 wt % to less than 40, 35, 30, 25, 20, 15, 10, 9, 8, 7, 6, 5 wt % as long as the films are provided with radio-opacity for making the device visible by means of fluoroscopy, for example, during the deployment procedure.

In the films, the radiopacifier may often be less concentrated compared to the support structures to avoid any affecting of the physical properties of the polymers or copolymers. In other parts of the occlusion device, for example in the waist portion or the proximal or distal support structures, the amount of radiopacifier may be increased because a higher stiffness of the waist portion or the support structures is suitable and the visibility of the occlusion device may simultaneously be improved. For example, varying amounts of $BaSO_4$ may be used in various parts of the occlusion device to enhance stiffness and non-stickiness. The proximal occlusion films of the occlusion device may, for example, be solution casted or hot-pressed with an amount of $BaSO_4$ ranging from about 0 wt % to about 40 wt %. The waist portion may, for example, be made of a biodegradable polymer having about 0 wt % to about 40 wt % $BaSO_4$. Either of, or both the proximal and the distal support structures may, on the other hand, contain about 1 wt % to about 40 wt % $BaSO_4$.

In another embodiment of the first aspect, the occlusion device additionally comprises a delivering system. In the context of the application, the term "delivering system" means a system which is suitable to deliver the occlusion device to the desired place in the body of a subject, like a mammal (including, e.g., primates including humans, rodents such as mice and rats, and ungulates such as pigs and the like) to be treated. The delivering system, however, does usually not be part of the device maintaining in the body of a patient, but may be removed at the end of the deployment procedure of the occlusion device.

The delivering system may comprise a sheath and a delivering means adapted to move the occlusion device through the sheath. In various embodiments, the delivering means is a rod removably connected to the distal support structure or to the proximal support structure. In the context of the invention, the term "removably connected" means that it can be removed from the occlusion device after the occlusion device has been positioned. The delivering means can move the occlusion device through the sheath for example, by pulling or pushing it from the distal end of the sheath.

The distal support structure and/or the proximal support structure may comprise a coupling means adapted for connecting the respective support structure with the rod. In various embodiments, the coupling means is a threaded interior surface of the distal support structure or the proximal support structure. The rod may, for example, be engaged with the distal support structure or the proximal support structure by means of a screwing mechanism, or a quick fit mechanism. In various embodiments, the rod comprises a threaded exterior surface to engage with the threaded interior surface of the distal support structure or the proximal support structure.

In other embodiments, the coupling means is a loop connected to the distal support structure. The rod may comprise a forceps to engage with the loop connected to the distal support structure. FIGS. 14 and 15 depict such an embodiment. Referring to FIG. 14, a loop (351) is attached to the scaffold (350) via distal support structure (20). The delivering means (301) is in the form of a rod (305) comprising a forceps (302) to removably engage with the loop (351). In FIG. 15, the forceps (302) is disengaged with the loop (351), thereby disconnecting the delivering means from the scaffold.

Since the delivering system generally does not come into contact with the body and is usually completely removed after insertion of the occlusion device into the sheath of a catheter, the delivering system may be formed of any suitable material, such as a metal, a polymer, ceramic or wood, and does not need to be formed of a biodegradable material.

The sheath can be a hollow polymeric tube adapted to house the folded occlusion device and the delivering means. The sheath can be inserted into a catheter for delivering the occlusion device to the tissue defect of the patient.

The above described occlusion device of the first aspect including the above described delivering system can be preloaded in a sheath, or can be prepared for preloading the occlusion device and the delivering system shortly before the deployment procedure is applied. Generally, the occlusion device is provided in a package which can then be sterilized. The sterilization can be carried out by any conventional process as long as the package with the occlusion device is sufficiently sterilized. An example of such conventional sterilization processes is ethylene oxide (ETO) sterilization in a standard ETO sterilization pouch. The occlusion device with or without the delivering system can be sealed in a package and then over at least 6 hours purged with ETO at about 37° C., usually followed by additional ethylene oxide (ETO) purging of ETO gas at ambient temperatures. The additional purging step can be 5 hours or more, such as 6, 7, 8, 9, 10, 12, 14, 16, 18, 20, 22, 24 hours, especially about 16 hours. Therefore, in one embodiment of the first aspect, the occlusion device is provided in a sterilized package.

In a second aspect, the invention refers to a method of closing an anatomical defect in a tissue comprising a conduit connecting an opening on a first tissue and an opening on a second tissue.

In this context, the term "closing an anatomical defect" may mean a surgical treatment of a patient in need of such a treatment, or may be an in vitro method where defects at tissues outside the patient are treated. The method of the second aspect of the invention comprises moving the sheath containing the occlusion device through the opening on the second tissue, the conduit, and the opening on the first tissue; moving the proximal support structure of the occlusion device out of the sheath through the opening on the first tissue by using a delivering means; deploying the proximal support structure at the front side of the first tissue (for example, the aorta side) to close the defect from the front side; withdrawing the sheath to release a portion of the waist portion of the occlusion device in the opening and to release the distal support portion and the remaining portion of the waist portion in the conduit; and deploying the distal support structure of the occlusion device in the conduit to anchor the device. The method according to the second aspect may include disconnecting the delivering means and moving the delivering means out of the conduit.

In the context of the present application, the term "moving" means pulling or pushing the device at its distal support portion or its proximal support portion (depending on the connection point of the delivering means with the scaffold) during insertion of the occlusion device into the sheath, withdrawal of the occlusion device out of the sheath, or in the proximity of the tissue of the subject to be treated. As mentioned above, the delivery means may be in the form of a rod removably connected to the proximal support structure or to the distal support structure.

In the act of moving the occlusion device out of the sheath and through the opening on the first tissue to the front side of the tissue, it is either meant that the sheath goes through the opening while the proximal support structure is moved out of the sheath, or the sheath is at the front side of the tissue while the proximal support structure is moved out of the sheath.

In an embodiment of the method of this aspect, the proximal support structure may support a proximal occlusion film. In this case, the proximal occlusion film is moved together with the proximal support structure.

The method of closing an anatomical defect in a tissue comprising a conduit connecting an opening on a first tissue and an opening on a second tissue using an occlusion device of the first aspect which is covered by the second aspect of the present invention comprises in a particular embodiment which is shown in FIG. 2 to FIG. 10, the act of insertion, anchoring, optionally repositioning, sealing, and then retrieving the delivering system.

Figure 2:
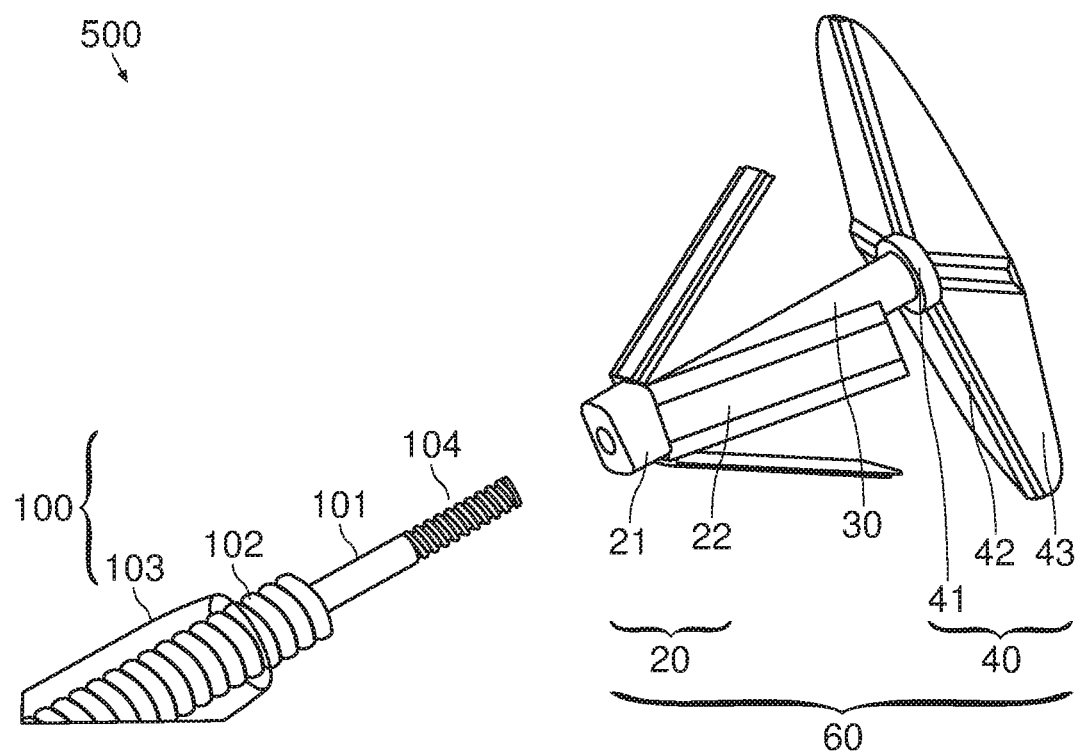
FIG. 2 shows a perspective view of an occlusion device according to an embodiment of the invention in an unassembled state.

In FIG. 2, the procedure is described on the basis of an in vivo method, wherein an opening in aorta wall ("first tissue") is closed. The method generally comprises the following:

1) Device Preparation

Referring to FIG. 2, the occlusion device (500) comprising a scaffold (60) and a delivering system (100) is shown. The scaffold (60) comprises a proximal support structure (40), a distal support structure (20), and a waist portion (30). The proximal support structure (40) comprises at least two arms, in the form of a plurality of spokes (42) outwardly extending from the middle (41) of the proximal support structure (40). In the embodiment shown, a proximal occlusion film (43) is supported by the proximal support structure (40), whereby the proximal occlusion film (43) is expanded between the spokes (42) of the proximal support structure (40). The distal support structure (20) comprises at least two arms, in the form of a plurality of spokes (22) outwardly extending from the middle (21) of the distal support structure (20). The waist portion (30) connects the proximal support structure (40) with the distal support structure (20).

The delivering system (100) comprises a delivering means (101) and a sheath (103). The delivering means (101) is in the form of a rod for removably connecting to the proximal support structure (40) or to the distal support structure (20). As depicted in the figure, the rod comprises a threaded exterior surface (104) to engage with the threaded interior surface (not shown) of the proximal support structure (40) or the distal support structure (20). (102) denotes a reinforced rod housing.

The occlusion device (500) may be provided in an unassembled state, i.e. the scaffold (40) is not connected with the delivering system (20). The occlusion device (500) may also be provided in an assembled state such as that shown in FIG. 3. In the embodiment shown in FIG. 3, the delivering means (101) is removably connected to the scaffold (60), which may take place via the proximal support structure (40) or the distal support structure (20). By moving the delivering means, the occlusion device may be loaded into a sheath (103).

2) Insertion

The delivering means (101) is used to push the occlusion device in a folded state into and to the end of the sheath (103) of a catheter, beginning with the proximal support structure, followed by the waist portion and the distal support structure into the sheath (103). The sheath (103) used in this embodiment can be, for example, a sheath usually used for heart catheter applications like a 6-8F sheath.

After the entire occlusion device has been inserted into the sheath (103), the sheath containing the occlusion device may be moved through the opening on the second tissue, the conduit and the opening on the first tissue such as that shown in FIG. 4. In so doing, the sheath (103) advances across the opening so that the proximal support structure and the proximal occlusion film may be pushed through the defect via the sheath (103) to the front side of the first tissue, as shown in FIG. 5.

3) Anchoring

After the proximal support structure and the proximal occlusion film have been pushed through the defect to the front side of the first tissue, the proximal support structure may be released from the sheath (103). The proximal support structure may spring open, for example, to its originally unfolded shape due to the shape memory property of the material of the support structure, and, thereby, unfolds the proximal occlusion film. This is depicted in FIG. 6. Thereafter, the sheath (103) is pulled back until the unfolded proximal support structure and the proximal occlusion film have been anchored at the front side, thereby sealing the defect from the front side of the septum, such as that shown in FIG. 7.

4) Reposition

If, for some reason, the occlusion device should be repositioned, the sheath (103) may be held in position while the delivering means (101) may be moved back, e.g. by pulling action, to force the occlusion device back into the sheath. The sheath may then be re-deployed upon repositioning.

5) Sealing

If the anchoring is satisfactory, the sheath (103) is withdrawn further to release the waist portion and the distal support structure from the sheath as shown in FIG. 8. The waist portion is brought within the opening and the distal support structure is allowed to spring automatically open as shown in FIG. 9. This can, for example, be managed by a sufficient rigidity of the material and the respective stress in the folded state or by shape memory properties of the respective support structure material. The distal support structure automatically opens its folded parts and is deployed in the conduit to anchor the device.

6) Removal of Delivering System

The delivering means (101) may be disconnected from the scaffold by unscrewing the delivering means (101) from the proximal or the distal support structure. The delivering means (101) and the sheath (103) may be pulled back to retrieve all parts of the delivering system and to leave the occlusion device in its folded working structure locked by means of the proximal support structure and the distal support structure provided at the front side of the first tissue and the conduit, respectively.

It is also within the above definition of the invention according to a third aspect, to use the occlusion device of the first aspect or a method according to the second aspect in a transcatheteral closure of an anatomical defect in tissue like a septal defect or shunt in the heart or the vascular system. Septal defect can be in this context any defect including, but being not limited to, atrial septal defects, ventricular septal defects, patent ductus arteriosus, or patent foramen ovale.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. An occlusion device for closing an anatomical defect in tissue that includes a conduit connecting an opening on a first tissue and an opening on a second tissue, the occlusion device comprising:

a scaffold that includes:
 a proximal support structure comprising at least two arms;
 a distal support structure comprising a threaded interior surface and at least two arms, wherein a tip of a free end of each of the respective arms of the distal support structure is adapted to contact a conduit wall of the conduit to provide anchorage for the distal support structure within the conduit; and
 a waist portion configured to extend through the opening on the first tissue and connect the proximal support structure with the distal support structure, and a delivering system that includes:
 a sheath;
 a rod comprising a threaded exterior surface; and
 a reinforced rod housing surrounding the rod and extending longitudinally along the rod, wherein the threaded exterior surface of the rod is engaged with the threaded interior surface of the distal support structure for moving the scaffold through the sheath, wherein, when the entire scaffold is in the sheath, the rod is engaged to the distal support structure with a longitudinal end of the reinforced rod housing directly abutting the distal support structure as the rod moves the scaffold through the sheath, wherein, when in the sheath, the at least two arms of the proximal support structure are folded at respective inner ends in an outward direction away from the waist portion, and the at least two arms of the distal support structure are folded at respective inner ends in an inward direction in the direction of the waist portion, and wherein the scaffold consists essentially of at least one biodegradable polymer, wherein the proximal support structure and the distal support structure comprise polycaprolactone (PCL), poly-(D,L-lactide-co-caprolactone) (PLC), or a mixture thereof.

2. The occlusion device according to claim 1, wherein the scaffold further comprises a proximal occlusion film supported by the proximal support structure.

3. The occlusion device according to claim 1, wherein the at least two arms of the proximal support structure are three or more spokes outwardly extending from a middle of the proximal support structure and having the respective inner ends connected with each other.

4. The occlusion device according to claim 1, wherein the at least two arms of the distal support structure are three or more spokes outwardly extending from a middle of the distal support structure and having the respective inner ends connected with each other.

5. The occlusion device according to claim 1, wherein:
 the at least two arms of the proximal support structure include 2 to 8 spokes outwardly extending from a middle of the proximal support structure and having the respective inner ends connected with each other; and
 the at least two arms of the distal support structure include 2 to 8 spokes outwardly extending from a middle of the distal support structure and having the respective inner ends connected with each other.

6. The occlusion device according to claim 1, wherein the distal support structure includes a middle and the at least two arms of the distal support structure are adapted to provide anchorage for the device in the tissue by outwardly extending from the middle of the distal support structure and contacting a wall of the conduit.

7. The occlusion device according to claim 1, wherein the scaffold includes a proximal occlusion film that is supported by the proximal support structure and expands between the at least two arms of the proximal support structure.

8. The occlusion device according to claim 1, wherein the proximal support structure, the distal support structure and the waist portion are integrally formed.

9. The occlusion device according to claim 1, wherein the biodegradable polymer is selected from the group consisting of polycaprolactone (PCL), poly-(D,L-lactide-co-caprolactone) (PLC), poly-L-lactide (PLLA), poly-D-lactide (PDLA), polyglycolide (PGA), polylactic acid (PLA), polycaprolactone-polylactic acid copolymer (PCL-PLA copolymer), polylactide-polyglycolide copolymer (PLGA), poly(trimethylene carbonate) (TMC); copolymers of polycaprolactone (PCL) and poly(trimethylene carbonate) (TMC); triblock copolymers of polylactic acid (PLA), polycaprolactone (PCL) and/or poly(trimethylene carbonate) (TMC); polylactic acid-polyethylene oxide copolymers, polygluconate polyhydroxybutyrate, polyanhydride, polyphosphoester, poly(amino acids), polydioxanone, cellulose, collagen, chitosan, and mixtures thereof.

10. The occlusion device according to claim 9, wherein the scaffold further comprises a proximal occlusion film supported by the proximal support structure and wherein one or more elements selected from the group of the proximal support structure, the proximal occlusion film, the distal support structure, and the waist portion comprise a radiopacifier.

11. The occlusion device according to claim 10, wherein the proximal support structure and the distal support structure comprise respective radiopacifiers.

12. The occlusion device according to claim 10, wherein the radiopacifier comprises barium sulfate.

13. The occlusion device according to claim 10, wherein the amount of radiopacifier comprised in either of, or both, the proximal occlusion film and waist portion ranges from about 0 wt % to about 40 wt %.

14. The occlusion device according to claim 10, wherein the amount of radiopacifier comprised in either of, or both, the proximal support structure and the distal support structure ranges from about 1 wt % to about 40 wt %.

15. The occlusion device according to claim 1, wherein the waist portion consists essentially of a biodegradable polymer selected from the group consisting of polycaprolactone (PCL), poly-(D,L-lactide-co-caprolactone) (PLC), poly-L-lactide (PLLA), poly-D-lactide (PDLA), polyglycolide (PGA), polylactic acid (PLA), polycaprolactone-polylactic acid copolymer (PCL-PLA copolymer), polylactide-polyglycolide copolymer (PLGA), poly(trimethylene carbonate) (TMC); copolymers of polycaprolactone (PCL) and poly(trimethylene carbonate) (TMC); triblock copolymers of polylactic acid (PLA), polycaprolactone (PCL) and/or poly(trimethylene carbonate) (TMC), and mixtures thereof.

16. The occlusion device according to claim 1, wherein the proximal support structure is more flexible than the remainder of the scaffold.

17. The occlusion device according to claim 1, wherein the proximal support structure has shape memory.

18. The occlusion device according to claim 17, wherein the proximal support structure elastically deforms in response to an applied force, and returns to more than 50% of its original shape upon release of the applied force.

19. The occlusion device according to claim 1, wherein the scaffold further comprises a proximal occlusion film supported by the proximal support structure and wherein one or more elements selected from the proximal support structure, the proximal occlusion film, the distal support structure, and the waist portion comprise a therapeutically active agent.

20. The occlusion device according to claim 19, wherein the therapeutically active agent is present as a coating on the proximal occlusion film.

21. The occlusion device according to claim 19, wherein the therapeutically active agent is selected from the group consisting of a drug, an antibiotic, an anti-inflammatory agent, an anti-clotting factor, a hormone, a nucleic acid, a peptide, a cellular factor, a growth factor, a ligand for a cell surface receptor, an anti-proliferation agent, an anti-thrombotic agent, an antimicrobial agent, an anti-viral agent, a chemotherapeutic agent, and an anti-hypertensive agent.

22. The occlusion device according to claim 21, wherein the therapeutically active agent comprises a drug, a protein, a growth factor, or combinations thereof.

23. The occlusion device according to claim 22, wherein the protein is selected from the group consisting of elastin, collagen, fibronectin, laminin, and mixtures thereof.

24. The occlusion device according to claim 22, wherein the growth factor is basic fibroblast growth factor, platelet-derived growth factor, or a mixture thereof.

25. The occlusion device according to claim 16, wherein the rod is removably connectable to the distal support structure or to the proximal support structure.

26. The occlusion device according to claim 25, wherein the proximal support structure comprise a threaded interior surface for connecting the proximal support structure with the rod.

27. The occlusion device according to claim 26, wherein the threaded exterior surface of the rod is configured to engage with the threaded interior surface of the proximal support structure.

28. The occlusion device according to claim 1 provided in a sterilized package.

29. A method, comprising:
  closing an anatomical defect in a tissue having a conduit connecting an opening on a first tissue and an opening on a second tissue, the closing:
  a) providing a sheath of a delivering system of an occlusion device into which a scaffold of the occlusion device has been inserted into the sheath, the scaffold being configured to close the anatomical defect in tissue that includes the conduit connecting the opening on the first tissue and the opening on the second tissue, the scaffold including:
    i) a proximal support structure comprising at least two arms;
    ii) a distal support structure comprising a threaded interior surface and at least two arms, wherein a tip of a free end of each of the respective arms of the distal support structure is adapted to contact a conduit wall of the conduit to provide anchorage for the distal support structure within the conduit; and
    iii) a waist portion configured to extend through the opening on the first tissue and connect the proximal support structure with the distal support structure, wherein, when in the sheath, the at least two arms of the proximal support structure are folded at respective inner ends in an outward direction away from the waist portion, and the at least two arms of the distal support structure are folded at respective inner ends in an inward direction in the direction of the waist portion, and wherein the scaffold consists essentially of at least one biodegradable polymer, wherein the proximal support structure and the distal support structure comprise polycaprolactone (PCL), poly-(D,L-lactide-co-caprolactone) (PLC), or a mixture thereof, b) moving the sheath containing the scaffold through the opening on the second tissue, the conduit, and the opening on the first tissue, c) moving the proximal support structure of the scaffold out of the sheath through the opening on the first tissue by using a rod of the delivering system, the rod comprising a threaded exterior surface engaged with the threaded interior surface of the distal support structure for moving the scaffold, wherein a reinforced rod housing surrounds the rod and extends longitudinally along the rod, wherein, when the entire scaffold is in the sheath, the rod is engaged to the distal support structure with a longitudinal end of the reinforced rod housing directly abutting the distal support structure as the rod moves the scaffold through the sheath, d) deploying the proximal support structure at a front side of the first tissue to close the defect from the front side, e) withdrawing the sheath to release a portion of the waist portion of the scaffold in the opening and to release the distal support portion and the remaining portion of the waist portion within the conduit, and f) deploying the distal support structure of the scaffold within the conduit to anchor the distal support structure within the conduit.

30. The method according to claim 29, wherein the rod is removably connected to the distal support structure.

31. The method according to claim 30, further comprising disconnecting the rod and moving the rod out of the conduit.

32. The method according to claim 29, wherein the closing includes closing a septal defect or shunt in a heart or a vascular system.

33. The method according to claim 32, wherein the septal defect is selected from the group consisting of atrial septal defects, ventricular septal defects, patent ductus arteriosus, and patent foramen ovale.

* * * * *